United States Patent [19]

Diaz et al.

[11] Patent Number: 4,683,347

[45] Date of Patent: Jul. 28, 1987

[54] GLYCERINE PURIFICATION PROCESS

[75] Inventors: Zaida Diaz, Houston; James H. Miller, Katy, both of Tex.

[73] Assignee: Shell Oil Company, Houston, Tex.

[21] Appl. No.: 877,051

[22] Filed: Jun. 23, 1986

[51] Int. Cl.⁴ .................... C07C 29/86; C07C 31/22
[52] U.S. Cl. .................................. 568/869; 568/859; 568/860
[58] Field of Search ........................................ 568/869

[56] References Cited

U.S. PATENT DOCUMENTS 2,081,721  5/1937  Van Dijck et al. ............... 568/869
2,154,930  4/1939  Evans .............................. 568/869
4,345,976  8/1982  Peter et al. ...................... 568/869
4,360,407  11/1982  Reierson ......................... 568/869

FOREIGN PATENT DOCUMENTS 2059787  4/1981  United Kingdom ............... 568/869

*Primary Examiner*—J. E. Evans
*Attorney, Agent, or Firm*—Ronald R. Reper

[57] ABSTRACT

The level of impurities such as glycerol-based acetals and/or ketals in glycerine, particularly glycerol-dimethylketal, is reduced by extraction of the glycerine with supercritical or near critical carbon dioxide.

13 Claims, No Drawings

GLYCERINE PURIFICATION PROCESS

BACKGROUND OF THE INVENTION

The present invention relates to a process for refining glycerine, and more particularly to a process for reducing the levels of impurities such as glycerine-based acetals and ketals, and particularly 4-hydroxymethyl-1,3-dioxanes; 5-hydroxymethyl-1,3-dioxolanes and 4-hydroxymethyl-1,3-dioxolanes, (hereinafter collectively referred to as acetals and/or ketals) in glycerine.

Glycerine, also referred to as glycerol, i.e. 1,2,3-propanetriol, has been a chemical of commerce for many years. Derived both as by-product from soap manufacture and synthetically, glycerine is used in many diverse applications, such as in alkyd resins, cellophane, tobacco processing, drugs, cosmetics, and in food and beverages.

There are three major routes to synthetic glycerine, each starting with propylene. One route involves four process steps—the chlorination of propylene to allyl chloride, the chlorohydrination of allyl chloride to glycerol dichlorohydrins, the hydrolysis of the dichlorohydrins to epichlorohydrin, and the hydrolysis of epichlorohydrin to glycerine. A second route is based upon three process steps—the oxidation of propylene to acrolein, the hydrogenation of acrolein to allyl alcohol, and the hydroxylation of allyl alcohol to glycerine. The third route also employs three steps—the epoxidation of propylene to propylene oxide, isomerization of propylene oxide to allyl alcohol, and the hydroxylation of the allyl alcohol to glycerine.

A number of methods for purifying glycerine of small amounts of undesirable compounds have been proposed over the years including e.g., catalytic hydrogenation in an acid medium, and treatments with chemicals such as hydrogen peroxide, with sulfuric acid and activated carbon, and with sodium carbonate. Further the concentration and/or purification of glycerine by extraction with certain solvents is known, e.g. the use of certain hydrocarbons, ethers, esters and chlorinated solvents is disclosed in U.S. Pat. No. 2,154,930; the use of tert-amyl alcohol is disclosed in U.S. Pat. No. 2,436,209 and the use of solvents including certain aliphatic alcohols, aromatic alcohols, cyclic amines, ketones, ethers, aldehydes, and esters is disclosed in U.S. Pat. No. 2,479,041. A distillative process for separating glycerine from certain acetals and/or ketals is disclosed in U.S. Pat. No. 4,360,407.

Applicants have found that some commercially available glycerine contains small amounts of acetals and/or ketals, which acetals and/or ketals should desirably be removed to very minimal levels for some applications. They have further discovered a relatively simple extraction process with a unique solvent to accomplish this.

SUMMARY OF THE INVENTION

The invention provides a process for reducing the level of acetals and/or ketals in glycerine which contains actals and/or ketals, which process comprises (a) extracting said glycerine in an extraction zone with $CO_2$ at conditions above or near the critical point of $CO_2$ to obtain (1) an extract comprising $CO_2$, acetals and/or ketals, and a minor amount of glycerine, and (2) glycerine having reduced acetals and/or ketals content, and (b) separating said extract from said glycerine having reduced acetals and/or ketals content.

DESCRIPTION OF PREFERRED EMBODIMENTS

The solvent employed in the extraction process of the invention is carbon dioxide at conditions above or near the critical point (87.9F and 1071 psia). The $CO_2$ is preferably dry, but moist $CO_2$ containing up to about its saturation point of water may be used. The water content of the glycerine may impact the selectivity of the $CO_2$ for the acetals and/or ketals; optimal moisture contents will be determined economically by comparing the costs associated with drying of the $CO_2$ or glycerine to various low levels of moisture content and the impact of moisture on selectivity for the acetals and/or ketals. Where the acetals and/or ketals removed from the glycerine are to be further purified for such applications as a functional fluid, solvent or plasticizer, it may be preferred to employ both relatively dry $CO_2$ and glycerine. Procedures for drying moist $CO_2$, if desired, are disclosed e.g., in U.S. Pat. No. 4,492,592; U.S. Pat. No. 4,492,593 and U.S. Pat. No. 4,500,333 (all incorporated herein by reference).

The present invention comprises reducing the level of acetals and/or ketals in glycerine containing-acetals and/or ketals by fluid-liquid extraction with $CO_2$ in one or more extraction steps so that two phases are formed in which the acetals and/or ketals to glycerine ratios are substantially different from each other. The $CO_2$ solvent fed to the extraction zone will typically have a density in the range above 30 pounds per cubic foot, preferably in the range from about 32 to about 62 pounds per cubic foot and most preferably from about 50 to about 60 pounds per cubic foot.

In extracting the acetals and/or ketals-containing glycerine, the conditions of the extraction may be varied, e.g., temperature, quantity of solvent employed, and the number of contacts between the solvent and the glycerine. Any known type of equipment and mechanical details of operation may be employed. The extraction may be intermittent or continuous, as is best adapted to secure the most efficient results. In the extraction zone when employing columns, it is possible to use unpacked or packed towers having plates or baffles therein, or to use equipment such as a rotary-disc contactor. It is possible to pass the solvent or the disperse phase through the glycerine layer or to pass the glycerine layer through the $CO_2$ solvent. The extraction may be upflow, downflow, cocurrent or countercurrent. Settling areas may be provided at the top or bottom of the columns or suitable settling chambers may be provided external to the extraction equipment. Centrifugal means may be provided for accelerating separation of the phases from ether the continuous or multiple extraction systems. Preferably the $CO_2$ solvent is flowed upwardly through the glycerine.

The extraction may be carried out at temperatures in the range from about 20° C. to about 65° C., preferably in the range from about 25° C. to about 50° C.; and pressures in the range from about 1,070 to about 5,000 psia, and preferably in the range from about 1200 to about 4000 psia. In the extraction zone it is preferred that the $CO_2$ fluid contacts the glycerine in a volume ratio of $CO_2$ to glycerine in the range from about 1:1 to about 50:1, and most preferably in the range from about 2:1 to about 20:1. When the $CO_2$ solvent is dispersed through the glycerine, preferably the $CO_2$ dispersed phase has a linear velocity in the extraction zone in the range from about 20 to about 200 feet per hour.

From the extraction zone the acetals and/or ketals-fat fluid $CO_2$ extract is an upper phase readily withdrawn from the glycerine.

In a preferred embodiment the acetals and/or ketals (and some glycerine) are separated from the $CO_2$ solvent by reducing the density of said $CO_2$ to below about 29 pounds per cubic foot to leave the extracted portion of the glycerine as residue. The density reduction may be accomplished in either of two ways, namely by lowering the pressure of the extract, or by heating of the extract. After such separation the $CO_2$ may be subjected to conditions above or near its critical point, and recycled to the extraction zone. In a particularly preferred embodiment the density of the extract from the extraction zone is reduced by at least about 25 pounds per cubic foot to leave the residue; e.g., from about 50 pounds per cubic foot in the extraction zone to about 25 pounds per cubic foot in order to recover the acetals and/or ketals from the fluid $CO_2$.

The invention is further illustrated but is not intended to be limited by the following examples.

EXAMPLE I

Into a high pressure stainless steel vessel having a visibility window (a Jerguson gauge) was added 35 ml of reagent grade glycerine obtained from Eastman Kodak Co. which glycerine was found by gas-liquid chromatographic analysis to contain about 0.11% by weight of acetals and/or ketals, particularly glycerol-dimethylketal, i.e. 2,2-dimethyl-4-hydroxymethyl-1,3-dioxolane. $CO_2$ was then added to a pressure of about 1215 psia (1200 psig) to form a separate upper fluid phase. The contents were stirred for a period of about 10 hours at a temperature of about 24° C. (75° F.). An aliquot portion of the upper fluid phase was depressed to atmospheric conditions leaving a residue, and the residue by gas-liquid chromatagraphic analysis was found to contain 57% by weight of acetals and/or ketals and 43% by weight of glycerine (on a water-free basis). The observed selectivity for acetals and/or ketals removal was about 1200.

EXAMPLE II

Into a high pressure stainless steel vessel was added 95 ml of a different reagent grade glycerine (also from Eastman kodak Co.) containing 0.14% by weight of acetals and/or ketals, particularly glycerol dimethylketal. $CO_2$ at a pressure of about 1265 psia (1250 psig) and a temperature of about 24° C. (75° F.) was added near the bottom of the vessel to flow through the glycerine at a rate of 1.5 liters per minute. After exiting the vessel, the $CO_2$ fluid was depressured at a needle valve and the material released upon depressurization was collected in cold traps immersed in a mixture of dry ice and isopropyl alcohol and having a temperature of about $-72°$ C. Th experiment was discontinued after about 980 liters of $CO_2$ (at atmospheric conditions) had passed through the glycerine. The material in the cold traps consisted of 59.5% by weight acetals and/or ketals and 40.5% by weight glycerine (on a water-free basis). Analysis of the glycerine in the vessel at the end of the experiment revealed that the amount of acetals and/or ketals had been reduced to 0.09% by weight. From these data a selectivity of about 1600 can be calculated.

What is claimed is:

1. A process for reducing the level of acetals and/or ketals in glycerine which contains acetals and/or ketals, which process comprises:

(a) extracting said glycerine in an extraction zone with $CO_2$ at conditions above or near the critical point of $CO_2$ to obtain (1) an extract comprising $CO_2$, acetals and/or ketals and a minor amount of glycerine, and (2) glycerine having reduced acetals and/or ketals content, and (b) separating said extract from said glycerine having reduced acetals and/or ketals content.

2. A process as in claim 1 wherein step (a) the $CO_2$ has a density above about 30 pounds per cubic foot.

3. A process as in claim 1 wherein step (a) the $CO_2$ has a density in range from about 32 to about 62 pounds per cubic foot.

4. A process as in claim 1, wherein after step (b) the density of the extract is reduced to the range below about 29 pounds per cubic foot, to separate said $CO_2$ from a residue comprising acetals and/or ketals and glycerine.

5. A process as in claim 4, wherein said density of the extract is reduced by lowering the pressure of said extract.

6. A process as in claim 4, wherein said density of the extract is reduced by heating said extract.

7. A process as in claim 4, wherein the $CO_2$ having a density below about 29 pounds per cubic foot is subjected to conditions above or near its critical point, and is recycled to said extraction zone.

8. A process as in claim 1, wherein in the extraction zone the temperature is in the range from about 20° C. to about 65° C.

9. A process as in claim 1, wherein in the extraction zone the pressure is in the range from about 1,070 psia to about 5,000 psia.

10. A process as in claim 1, wherein in the extraction zone $CO_2$ is the dispersed phase contacting the glycerine at a dispersed phase linear velocity in the range from about 20 to about 200 feet per hour.

11. A process as in claim 1 wherein in the extraction zone the $CO_2$ contacts the glycerine in a volume ratio of $CO_2$ to glycerine from about 1:1 to about 50:1.

12. A process as in claim 11 wherein said volume ratio is in the range from about 2:1 to about 20:1.

13. A process for reducing the level of acetals and/or ketals in glycerine which contains acetals and/or ketals, which process comprises (a) extracting said glycerine in an extraction zone with supercritical $CO_2$ fluid having a density in the range above about 50 pounds per cubic foot to obtain (1) an extract having a density above about 50 pounds per cubic foot comprising $CO_2$, acetals and/or ketals, and a minor amount of glycerine, and (2) glycerine having reduced acetals and/or ketals content, (b) separating said extract from said glycerine having reduced acetals and/or ketals content, (c) reducing the density of said extract to a density value at least about 25 pounds per cubic foot lower than the density of said extract to afford (1) a residue comprising acetals and/or ketals and glycerine, and (2) $CO_2$ fluid having a density at least about 25 pounds per cubic foot lower than the density of said extract, (d) separating said $CO_2$ fluid from said residue, (e) subjecting said $CO_2$ fluid from step (d) to supercritical or near critical conditions to obtain a high density $CO_2$ fluid having a density of at least about 50 pounds per cubic foot, and (f) recycling said high density $CO_2$ fluid from step (e) to said extraction zone.

* * * * *